(12) United States Patent
Davis, III et al.

(10) Patent No.: US 8,211,141 B2
(45) Date of Patent: *Jul. 3, 2012

(54) STRETCH RESISTANT DESIGN FOR EMBOLIC COILS WITH STABILIZATION BEAD

(75) Inventors: Richard Champion Davis, III, Plantation, FL (US); Todd E. Goede, Alachua, FL (US); David A. Kilmer, North Miami, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/643,465

(22) Filed: Dec. 21, 2009

(65) Prior Publication Data

US 2010/0131003 A1 May 27, 2010

Related U.S. Application Data

(62) Division of application No. 11/395,704, filed on Mar. 31, 2006, now Pat. No. 7,766,933.

(51) Int. Cl.
*A61M 29/00* (2006.01)
*A61F 11/00* (2006.01)
(52) U.S. Cl. ............ 606/200; 606/108; 623/1.11
(58) Field of Classification Search .......... 606/200, 606/108; 623/1.11, 1.15
See application file for complete search history.

(56) References Cited

U.S. PATENT DOCUMENTS

| | | | |
|---|---|---|---|
| 5,108,407 A | 4/1992 | Geremia | |
| 5,122,136 A | 6/1992 | Guglielmi | |
| 5,304,195 A | 4/1994 | Twyford, Jr. | |
| 5,334,210 A | 8/1994 | Gianturco | |
| 5,382,259 A | 1/1995 | Phelps | |
| 5,853,418 A | 12/1998 | Ken | |
| 6,165,178 A | 12/2000 | Bashiri | |
| 6,193,728 B1 | 2/2001 | Ken | |
| 6,277,125 B1 | 8/2001 | Barry | |
| 6,280,457 B1 | 8/2001 | Wallace | |
| 6,964,671 B2 | 11/2005 | Cheng | |
| 7,166,122 B2 * | 1/2007 | Aganon et al. | 606/200 |
| 7,608,089 B2 | 10/2009 | Wallace | |
| 2004/0002733 A1 | 1/2004 | Teoh | |
| 2004/0034363 A1 | 2/2004 | Wilson | |
| 2005/0043755 A1 | 2/2005 | Wilson | |

* cited by examiner

*Primary Examiner* — Vy Q Bui

(57) ABSTRACT

A vasoocclusive embolic delivery system for use in placement of an embolic coil at a treatment site within a vessel. The embolic coil includes an elongated stretch resistant fiber having its distal end bonded to the distal end of the embolic coil. The stretch resistant fiber extends through a central lumen of the coil and extends beyond the proximal end of the coil. Also included is a generally cylindrical stabilization bead, having a diameter slightly smaller than the diameter of the central lumen of the coil, mounted on the stretch resistant fiber within the lumen of the embolic coil. The stabilization bead serves to keep the stretch resistant fiber centered within the lumen of the embolic coil. Additionally, a headpiece is mounted on the proximal end of the stretch resistant fiber and serves to couple the embolic coil to the delivery system.

10 Claims, 2 Drawing Sheets

STRETCH RESISTANT DESIGN FOR EMBOLIC COILS WITH STABILIZATION BEAD

CROSS REFERENCE TO RELATED APPLICATION

The present application is a divisional of U.S. patent application Ser. No. 11/395,704, filed Mar. 31, 2006 now U.S. Pat. No. 7,766,933.

BACKGROUND OF INVENTION

1. Field of the Invention

The present invention relates to a medical device designed for implantation within a vessel of the body, and more particularly, to a stretch resistant vasoocclusive coil for the treatment of aneurysms. The vasoocclusive coil is particularly suited for use in cases where it may be necessary to reposition the coil once the coil has been initially placed within the vessel.

2. Description of the Prior Art

For many years, vasoocclusive devices have been used to occlude blood vessels at specific treatment locations. These devices take many different forms including helically wound coils, coils wound within coils or other such coil configurations. Examples of various coil configurations are disclosed in U.S. Pat. No. 5,334,210, entitled "Vascular Occlusion Assembly;" and U.S. Pat. No. 5,382,259, entitled, "Vasoocclusion Coil with Attached Tubular Woven or Braided Fibrous Covering." Embolic coils are generally formed of a radiopaque metallic material, such as platinum, gold, tungsten, or an alloy of these metals. Often, several coils are placed at a given location to occlude, or partially occlude, the flow of blood through the vessel or aneurysm by promoting thrombus formation at the particular location.

Flexible catheters have been used to place various devices or medications within the vasculature of the human body. Such devices or medications include dilation balloons, radiopaque fluids, liquid medications, and various types of occlusion devices such as balloons and embolic coils. Examples of such catheter-based devices are disclosed in U.S. Pat. No. 5,108,407, entitled "Method and Apparatus for Placement of an Embolic Coil;" and U.S. Pat. No. 5,122,136, entitled "Endovascular Electrolytically Detachable Guidewire Tip for the Electroformation of Thrombus in Arteries, Veins, Aneurysms, Vascular Malformations and Arteriovenous Fistulas." These patents disclose catheter-based devices designed to deliver embolic coils to a predetermined site within a vessel of the human body in order to treat aneurysms, or alternatively, to occlude a blood vessel at a particular location.

Additionally, embolic coils have been placed within the distal end of a catheter, such that when the distal end of the catheter is properly positioned, the coil may then be pushed out of the end of the catheter with a pusher member to release the coil at the predetermined site within the vessel. This procedure for placement of the embolic coil is conducted under fluoroscopic visualization, such that the movement of a coil through the vasculature of the body may be monitored, and the coil may be placed in the desired location.

To prevent stretching of the embolic device, especially during post-deployment retrieval, or repositioning during delivery, embolic devices often take the form of an embolic coil having a lumen extending therethrough and a stretch resistant member extending through the lumen. In one embodiment, the stretch resistant member takes the form of a fiber which is attached to the proximal and distal ends of the coil. In another embodiment, the stretch resistant member is fixedly attached to the distal end of the embolic coil, is extended through the lumen of the coil, and is detachably connected to a proximal end of an elongated pusher member. The connection between the pusher member and the coil may be severed by application of heat to the stretch resistant member, typically formed of a thermoplastic material. Such a device is disclosed in U.S. Patent Publication No. 2004/0034363, entitled "Stretch Resistant Therapeutic Device."

Another variation of a stretch resistant embolic device includes a helically wound outer coil with a stretch resistant member extending therethrough. In order to prevent stretching during movement of the coil, the stretch resistant member is fixedly attached to the coil in at least two locations, such as the proximal end and the distal end. The coil may take on a secondary shape when it is released from the delivery device. Such a device is disclosed in U.S. Pat. No. 5,853,418, entitled "Stretch Resistant Vaso-occlusive Coils (II)."

Yet another embodiment of a stretch resistant coil includes a stretch resistant member, such as a fiber, which extends through at least a portion of a primary coil having proximal and distal ends. The stretch resistant member is attached to the primary coil at two axially separated locations to prevent or minimize axial stretching of the coil. One of these attachment locations is created with an anchor assembly disposed within the lumen of the coil. The anchor assembly takes the form of a coil that is incorporated into the windings of the primary coil. Such a device is disclosed in US Patent Publication No. U.S. 2004/0002733, entitled "Integrated Anchor Coil in Stretch-Resistant Vaso-occlusive Coils."

Still another embodiment of a stretch resistant coil and delivery system takes the form of an interlocking coupling between a pusher member and a thin wire affixed to an embolic coil. The thin wire may be affixed to a distal, intermediate or proximal location on the coil and includes a ball shaped member fixedly attached to the proximal end of the wire. In order to position the coil at the treatment site, a pusher member with a ball member affixed to its distal end releasably interlocks with the ball member at the proximal end of the stretch resistant member. Such a device is disclosed in U.S. Pat. No. 5,304,195, entitled "Detachable Pusher-Vasoocclusive Coil Assembly with Interlocking Coupling."

Even another embodiment of a stretch resistant embolic coil includes a coil with proximal and distal ends reinforced with a stretch resistant member extending therethrough. The distal end of the stretch resistant member is fixedly attached at the distal end of the coil, and the proximal end of the stretch resistant member is detachably mounted on an elongated pusher member at its distal end. Such a device is disclosed in U.S. Patent Publication No. 2005/0043755, entitled, "Vasoocclusive Coil with Enhanced Therapeutic Strand Structure."

Yet another embodiment of a stretch resistant embolic coil includes a wire that is wrapped with a polymer and is helically wound. A stretch resistant member may extend though the lumen of the coil and is attached to at least two points on the coil. Such a device is disclosed in U.S. Pat. No. 6,280,457, entitled, "Polymer Covered Vaso-occlusive Devices and Methods of Producing Such Devices."

Still another embodiment of a stretch resistant embolic coil includes a primary helically wound coil with a lumen therethrough. One or more stretch resistant members extend through the lumen of the coil. The stretch resistant members are attached at two or more locations on the coil. Such a device is disclosed in U.S. Pat. No. 6,193,728, entitled, "Stretch Resistant Vaso-occlusive Coils (II)."

SUMMARY OF THE INVENTION

The present invention is directed toward a vasoocclusive device deployment system for use in placing an embolic coil at a preselected site within a vessel. In accordance with an aspect of the present invention, the deployment system includes an elongated flexible delivery catheter and an elongated flexible deployment catheter slidably disposed within the lumen of the delivery catheter. Also included is the embolic coil, which preferably is helically wound and has a closed pitch. An elongated stretch resistant fiber, preferably formed of nitinol is bonded to the distal end of the coil, and extends through the lumen of the coil to a point proximal of the proximal end of the embolic coil. In order to maintain alignment of the coil about the stretch resistant fiber, a generally cylindrical stabilization bead, having an outer diameter slightly smaller than the diameter of the lumen of the embolic coil, is mounted on the stretch resistant fiber at a location in proximity to the proximal end of the embolic coil.

In accordance with another aspect of the present invention, a headpiece is mounted on the proximal end of the stretch resistant fiber and is also disposed in fluid tight engagement within the lumen of the distal section of the deployment catheter. Additionally, a source of fluid pressure is coupled to the proximal section of the deployment catheter for applying a fluid pressure to the headpiece to thereby release the embolic coil from the deployment catheter. The distal section of the deployment catheter may be formed of a material which exhibits the characteristic that when fluid pressure is applied to the lumen of the deployment catheter the distal section of the deployment catheter expands outward, to release the headpiece.

In accordance with yet another aspect of the present invention, the stabilization bead extends longitudinally through only a portion of the lumen of the embolic coil. Also, the stabilization bead may include a longitudinal passageway extending therethrough, and the stretch resistant fiber then extends through the passageway.

In accordance with even another aspect of the present invention, an embolic device, includes an embolic coil preferably taking the form of a helically wound closed-pitch embolic coil. An elongated stretch resistant fiber, preferably formed of nitinol, is bonded to the distal end of the embolic coil and extends through the lumen of the coil to a point just proximal of the proximal end of the coil. In order to maintain the alignment of the coil about the stretch resistant fiber, a generally cylindrical stabilization bead, having an outer diameter slightly smaller than the diameter of the lumen of the embolic coil, is mounted on the stretch resistant fiber at a location in proximity to the proximal end of the embolic coil. The stabilization bead extends longitudinally through only a portion of the lumen of the embolic coil, and may include a longitudinal passageway extending therethrough, through which the stretch resistant fiber extends. Also included is a headpiece mounted on the proximal end of the stretch resistant fiber which serves to couple the coil to a delivery system.

In accordance with still another aspect of the present invention, an embolic coil, preferably takes the form of a helically wound closed-pitch embolic coil. An elongated stretch resistant fiber, preferably formed of nitinol, is attached to the distal section of the embolic coil at a location in proximity to the distal end of the embolic coil and may extend through the lumen of the coil. In order to maintain the alignment of the coil about the stretch resistant fiber, a generally cylindrical stabilization bead, having an outer diameter slightly smaller than the diameter of the lumen of the embolic coil, is mounted on the stretch resistant fiber at a location in proximity to the proximal end of the coil. The stabilization bead extends longitudinally through only a portion of the length of the embolic coil, and may include a longitudinal passageway extending therethrough, through which the stretch resistant fiber extends. Also included is a headpiece mounted on the proximal end of the stretch resistant fiber which serves to couple the coil to a delivery system.

These aspects of the invention and the advantages thereof will be more clearly understood from the following descriptions and drawings of a preferred embodiment of the present invention:

DESCRIPTION OF THE PREFERRED EMBODIMENT

Figure 1:
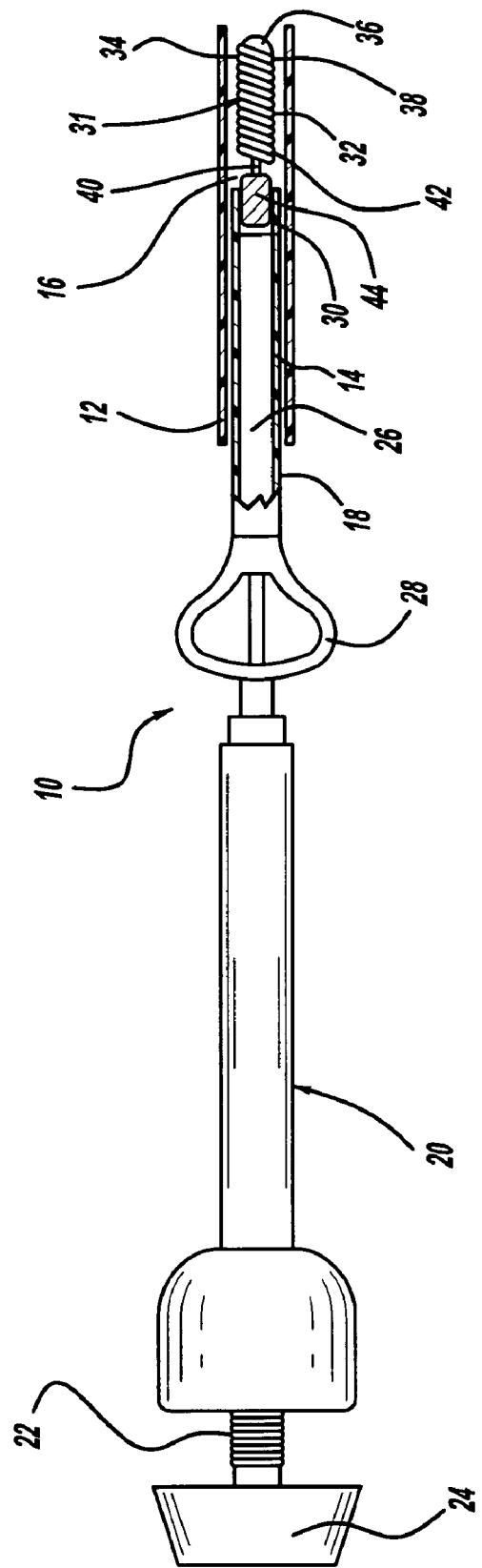
FIG. 1 is an enlarged, partially sectional view of one embodiment of a stretch resistant vasoocclusive device deployment system in accordance with the present invention; and, FIG. 2 is an enlarged sectional view of the stretch resistant embolic device shown in FIG. 1.

FIG. 1 generally illustrates one embodiment of a stretch resistant vasoocclusive device deployment system 10 of the present invention, including an elongated flexible delivery catheter 12 having an elongated flexible deployment catheter 14 slidably disposed within the lumen 16 of the delivery catheter 12 and a stretch resistant embolic device 31 situated within the lumen 26 of the distal section 30 of the deployment catheter 14. A source of fluid pressure is coupled to the proximal section 18 of the deployment catheter 14 and preferably takes the form of a syringe 20. The syringe 20 includes a threaded piston 22, which is controlled by a handle 24 to thereby infuse fluid into the lumen 26 of the deployment catheter 14. Also as illustrated, the proximal end 18 of the deployment catheter 14 includes a winged hub 28 which aides in the insertion of the deployment catheter into the vasculature of the body.

A stretch resistant embolic device 31 is disposed within the lumen 26 of the distal section 30 of the deployment catheter 14. The stretch resistant embolic device 31 includes an embolic coil 32 having an atraumatic distal bead 36 bonded to the distal end 38 of the coil 32. Also included is a stretch resistant fiber 40 which is attached to the proximal end of the atraumatic bead 36 and extends through the embolic coil 32 to a point beyond the proximal end 42 of the coil 32. Additionally, a headpiece 44 is attached to the proximal end of the stretch resistant fiber 40. In turn, the headpiece 44 is disposed in fluid tight engagement within the lumen 26 of the distal section 30 of the deployment catheter 14 thereby coupling the stretch resistant embolic device 31 to the deployment catheter 14.

When the embolic coil 32 is at the desired treatment site, the handle 24 is manipulated to advance the threaded piston 22 which thereby infuses fluid into the lumen of the deployment catheter 14. The fluid is advanced through the lumen 26 of the deployment catheter 14 and pressure is applied to the proximal end of the headpiece 44 thereby to displace it from its position within the distal section 30 of the deployment catheter 14.

If desired, the distal section 30 of the deployment catheter 14 may be formed from a material having a different durometer from that used to form the proximal section 18. For example, the proximal section 18 of the deployment catheter 14 may be formed of Pebax material having a durometer in the range of about 62 D to 75 D. The proximal section will then be sufficiently flexible to traverse the vasculature of the human body, but also sufficiently rigid such that when a fluid pressure of approximately 300 psi is applied to the interior of this section of the deployment catheter there is little, if any, radial expansion of the walls of this section of the deployment catheter. In contrast, the distal section 30 of the deployment catheter 14 may be formed from a polymer material with a relatively low durometer. The distal section 30 of the deployment catheter 14 is preferably formed from a block copolymer, such as Pebax, having a durometer in a range of 25 D to 55 D with a preferred durometer of 40 D.

The lower durometer material used to form the distal section 30 of the deployment catheter 14 exhibits the characteristic that when a fluid pressure of approximately 300 psi is applied to the interior, the walls of the distal end 30 expand radially, somewhat similar to the action of a balloon inflating, to thereby release the headpiece 44 of the embolic coil 32.

Figure 2:
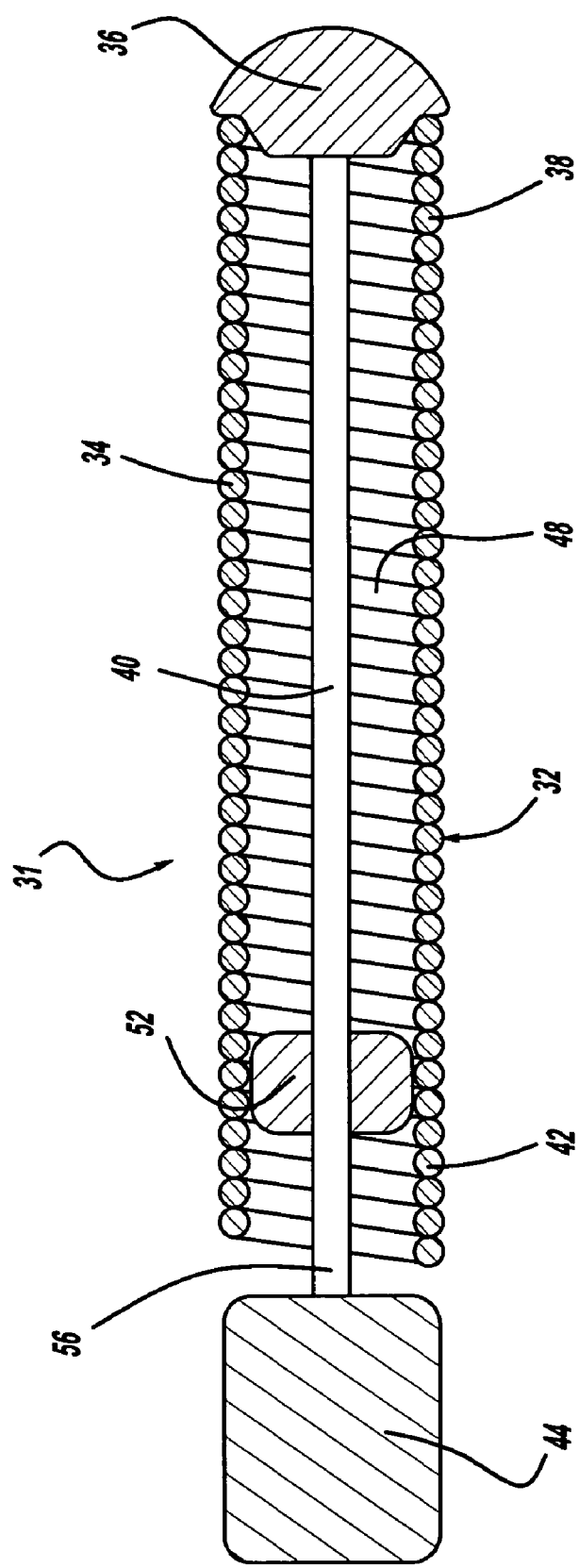

FIG. 2 illustrates in greater detail the stretch resistant embolic device 31 for placement at a treatment site. The stretch resistant embolic device 31 includes the embolic coil 32 which has the atraumatic distal bead 36 bonded to the distal end 38 of the coil 32. Also included is the stretch resistant fiber 40 which is attached to the proximal end of the atraumatic distal bead 36 and extends through the lumen 48 of the coil 32. The stretch resistant fiber 40 extends through a central passageway of the coil. A stabilization bead 52 is mounted on the stretch resistant fiber 40 within the proximal section of the embolic coil 32. The proximal end 56 of the stretch resistant fiber 40 extends to a point beyond the proximal end 42 of the coil 32 and is attached to the headpiece 44.

More particularly, the embolic coil 32 is preferably formed of helical turns 34 wound in a closed pitch configuration and is formed from a platinum tungsten alloy. The atraumatic distal bead 36 has a generally hemispherical shape and is formed from a plasma bead, or a solder weld. The stretch resistant fiber 40 is preferably formed from a nitinol wire, but may also be formed from a polymer braid, or filament. The stabilization bead 52 is formed from a metallic or polymeric material. Further, the outside diameter of the stabilization bead 52 is slightly less than the inner diameter of the lumen 48 of the coil 32 such that the stabilization bead 52 moves freely within the coil 32. The length of the stabilization bead 52 is on the order of the length of two or three of the helical turns 34 of embolic coil 32.

During placement of the coil 32, fluid pressure is applied to the headpiece 44 to dislodge the headpiece from the deployment device 10 at the treatment site. The distance between the headpiece 44 and the stabilization bead 52 is designed to be relatively short in order to prevent the stretch resistant fiber 40 from buckling when fluid pressure is applied to the headpiece 44. Even, if some buckling should occur, the headpiece is prevented from being pushed axially into the lumen of the coil 32 because the diameter of the headpiece 44 is slightly larger than that of the lumen 48 of the embolic coil 32. This construction allows the headpiece 44 to apply pressure evenly over the entire proximal end 42 of the coil 32, and therefore, the coil tends to be pushed in a straight line from the deployment device.

The stabilization bead 52 also provides for increased control and accuracy in placing the device 31, because the helical turns 34 of the embolic coil 32 remain equidistant from the stretch resistant fiber 40 along the length of the coil 32. Therefore, the coil 32 may be pushed in a straight line from the deployment catheter 14 increasing the accuracy of delivery to the treatment site.

Another important advantage of the present invention is that if it is determined that the embolic device 31 is improperly positioned, the embolic device may then be withdrawn from that location and placed at another location, or even removed from the body altogether. The stretch resistant fiber 40 facilitates repositioning of the coil 32 because the coil 32 is prevented from stretching when it is pulled proximally. The overall flexibility of the coil 32 is maintained, even with the added stretch resistance, because the stretch resistant fiber 40 is only in direct contact with the distal end 38 of the coil 32 and with slight contact with the coil through the stabilization bead. Additionally, the overall flexibility of the coil is further maintained, because the headpiece 44 is attached only to the stretch resistant fiber 40 and not directly to the embolic coil 32.

As is apparent, there are numerous modifications of the preferred embodiment described above which will be readily apparent to one skilled in the art, such as many variations and modifications of the embolic coil including numerous coil winding configurations. There are also variations in the materials used to form the various components. Additionally, the size, shape, and positioning of the stabilization bead may be modified as well. These modifications would be apparent to those having ordinary skill in the art to which this invention relates and are intended to be within the scope of the claims which follow.

That which is claimed is:

1. A vasoocclusive embolic device for use in placement at a treatment site within a vessel, comprising:
    an embolic coil having proximal and distal ends and a lumen extending therethrough;
    an elongated stretch resistant fiber having proximal and distal ends, said distal end of said stretch resistant fiber being bonded to the distal end of the embolic coil and extending through the lumen of the embolic coil to a point proximal of the proximal end of the coil;
    a generally cylindrical stabilization bead having an outer diameter slightly smaller than a diameter of the lumen of the embolic coil and being mounted on the stretch resistant fiber at a location in proximity to the proximal end of the embolic coil to maintain an alignment of the coil about the stretch resistant fiber; and,
    a headpiece mounted on the proximal end of the stretch resistant fiber which serves to couple the embolic coil to a delivery system.

2. A vasoocclusive embolic device as defined in claim 1, wherein the stabilization bead extends longitudinally through only a portion of the lumen of the embolic coil.

3. A vasoocclusive embolic device as defined in claim 1, wherein the stabilization bead includes a longitudinal passageway extending therethrough and the stretch resistant fiber extends through said passageway.

4. A vasoocclusive embolic device as defined in claim 1, wherein the stretch resistant fiber is formed of nitinol.

5. A vasoocclusive embolic device as defined in claim 1, wherein the embolic coil comprises a helically wound closed-pitch embolic coil.

6. A vasoocclusive embolic device for use in placement at a treatment site within a vessel, comprising:
    an embolic coil having proximal and distal ends and a lumen extending therethrough;
    an elongated stretch resistant fiber attached to a distal section of the coil at a location in proximity to the distal end of the embolic coil;

a generally cylindrical stabilization bead having an outer diameter slightly smaller than a diameter of the lumen of the embolic coil and being mounted on the stretch resistant fiber at a location in proximity to the proximal end of the embolic coil to maintain alignment of the coil about the stretch resistant fiber; and, a headpiece mounted on the proximal end of the stretch resistant fiber for coupling the embolic coil to a delivery system.

7. A vasoocclusive embolic device as defined in claim 6, wherein the stabilization bead extends longitudinally through only a portion of the lumen of the embolic coil.

8. A vasoocclusive embolic device as defined in claim 6, wherein the stabilization bead includes a longitudinal passageway extending therethrough, and the stretch resistant fiber extends through said passageway.

9. A vasoocclusive embolic device as defined in claim 6, wherein the stretch resistant fiber is formed of nitinol.

10. A vasoocclusive embolic device as defined in claim 6, wherein the embolic coil comprises a helically wound closed-pitch embolic coil.

* * * * *